United States Patent [19]

Schachar

[11] Patent Number: 4,886,815
[45] Date of Patent: Dec. 12, 1989

[54] TREATMENT AND PREVENTION OF RETINAL EDEMA WITH DOPAMINERGIC ANTAGONISTS

[76] Inventor: Ronald A. Schachar, P.O. Box 145, Denison, Tex. 75020

[21] Appl. No.: 922,925

[22] Filed: Oct. 24, 1986

Related U.S. Application Data

[60] Division of Ser. No. 725,101, Apr. 19, 1985, Pat. No. 4,624,957, and a continuation-in-part of Ser. No. 622,495, Jun. 20, 1984, abandoned.

[51] Int. Cl.$^4$ .................. A61K 31/445; A61K 31/54; A61K 31/38; A61K 31/34
[52] U.S. Cl. .................. 514/327; 514/211; 514/224.8; 514/437; 514/474
[58] Field of Search ........... 514/211, 224.8, 437, 514/912, 327, 474

[56] References Cited

U.S. PATENT DOCUMENTS

| | | | |
|---|---|---|---|
| 4,088,755 | 5/1978 | Inanaga et al. | 424/247 |
| 4,166,853 | 9/1979 | McCall | 424/258 |
| 4,201,706 | 5/1980 | Trager et al. | 514/912 |
| 4,443,441 | 4/1984 | Galin | 514/912 |
| 4,505,909 | 3/1985 | Bernstein | 514/912 |
| 4,620,979 | 11/1986 | Schachar | 514/912 |

FOREIGN PATENT DOCUMENTS

| | | | |
|---|---|---|---|
| 57-2279 | 1/1982 | Japan | 514/211 |
| 8203393 | 10/1982 | World Int. Prop. O. | 514/912 |

OTHER PUBLICATIONS

The Pharmacological Basis of Therapeutics, pp. 546-558—1966.
Investigative Ophthal. & Visual Sci., vol. 16 (5), May—1977—pp. 381-392.
Chem. Abst., 108:88048(d) (1988)—Scornil et al.
Chem. Abstr. 82:93297h (1975)—Tuck.
Chem. Abstr. 87:3625q (1977)—Tso et al.
Chem. Abstr. 88:32029z (1978)—Scatton et al.
Chem. Abstr. 89:12149f (1978)—Lapinet et al.
Chem. Abstr. 93:143069k (1980)—Magnistretti et al.
Chem. Abstr. 101:48632p (1984)—Chion.
Chem. Abstr. 101:108722s (1984)—Sears.
Fung, W. E., Ophthalmology 89(8), 898-901 (1982).
Jampol, L. M., Ophthalmology 89(8), 891-897 (1982).
Rebec, G. V. et al., Science 227, 438-440 (1985).
Remington's Pharmaceutical Sciences, 16th Ed., A. Osol, Ed., Mack Publishing Co., Easton, Pa., 1980, pp. 1029-1037.

Primary Examiner—Douglas W. Robinson
Assistant Examiner—Zohreh A. Fay
Attorney, Agent, or Firm—Vorys, Sater, Seymour and Pease

[57] ABSTRACT

Retinal edema, in particular cystoid macular edema, is prevented or treated by administering to the patient afflicted with retinal edema or in danger of experiencing retinal edema an amount of a dopaminergic antagonist effective to reduce the edema. A preferred dopaminergic antagonist is haloperidol. The activity of the dopaminergic antagonist may be potentiated by concurrent administration of ascorbic acid.

27 Claims, No Drawings

TREATMENT AND PREVENTION OF RETINAL EDEMA WITH DOPAMINERGIC ANTAGONISTS

This application is a divisional of co-pending application Ser. No. 725,101 filed on Apr. 19, 1985, now U. S. Pat. No. 4,624,957, which was a continuation-in-part of application Ser. No. 622,495, filed on June 20, 1984, now abandoned.

This application is a continuation-in-part of copending Application Serial No. 622,495, filed June 20, 1984.

BACKGROUND OF THE INVENTION

1. Field of the Invention:

This invention relates to pharmacological treatment and prevention of retinal edema and more particularly to treatment and prevenion of cystoid macular edema by administration of dopaminergic antagonists.

2. Description of the Prior Art:

Retinal edema is a physiological condition characterized by accumulation of excess fluid in the retina of the eye. A particularly troublesome type of retinal edema is cystoid macular edema (CME), a condition in which small cysts filled with a watery fluid form principally in the inner nuclear layer and outer plexiform layer of the retina, in and around the macula. Since the macular area of the retina is the location of the most acute vision, CME is particularly detrimental to vision. CME is associated with a number of diseases, e. g., hypertensive vascular diseases and diabetes. However, a paricularly difficult form of the disease is CME which follows successful cataract extraction. In a relatively high percentage of cases, cystoid macular edema develops some weeks after surgery, resulting in a deterioration of the vision which had been restored by successful cataract extraction. In most patients the condition gradually cleaars spontaneously, but in some it persists and affects their vision more or less permanently. The cause of CME is unknown, and hitherto there has been no certainly effective treatment for the condition.

A number of treatments have been proposed for alleviating CME after cataract surgery. Since it is believed that retinal trauma produced by tension on retinal attachments of the vitreous may be a cause of CME, cases of chronic CME have been treated with some success by surgical severing of vitreous strands attached to the surgical wound (Fung, W. E., Ophthalmology 89(8), 898–901 (1982)).

Because of the association of CME with inflammaatory conditions of the eye, topical and systemic anti-inflammatory drugs have been administered. Corticosteroids and non-steroid anti-inflammatories, e. g. ibuprofen, indomehacin, have been used, and have apparenly been of some use in alleviating the condition (Jampol, L. M., Ophthalmology 89(8), 891–897 (1982)). However, no completely reliable treatment for CME has been discovered hitherto.

Therefore a need has continued to exist for a method of treating and preventing retinal edema and particularly cystoid macular edema, which is effective and reliable.

SUMMARY OF THE INVENTION

Accordingly it is an object of this invention to provide a method of treating and preventing retinal edema.

A further object is to provide a method for treating and preventing cystoid macular edema.

A further object is to provide a pharmacological method for treating and preventing cystoid macular edema.

Other objects of the invention will become apparent from the description of the invention which follows.

The objects of the invention are achieved by a method for treatment and/or prevention of retinal edema which comprises administering to a patient in danger of being afflicted with retinal edema an amount of a dopaminergic antagonist effective to prevent the edema or reduce it. Ascorbic acid may be administered concurrently to potentiate the action of the dopaminergic antagonist.

DETAILED DESCRIPTION OF THE INVENTION AND PREFERRED EMBODIMENTS

Any dopaminergic anagonist is an effective drug for treating retinal edema, and particularly CME, by the process of this invention. Such drugs are well known to those skilled in the art and include reserpine and related rauwolfia alkaloids; phenothiazine derivatives frequently used as tranquilizers such as chlorpromazine, triflupromazine, mesoridazine, piperacetazine, thioridazine, acetophenazine, fluphenazine, perphenazine, trifluoperazine, and the like; thioxanthines, such as chlorprothixene, thiohixene, and the like; substituted butyrophenones such as haloperidol; dibenzoxazepines such as loxapine; and other dopaminergic antagonists, such as molindone, and the like. The compounds can be administered as the free compound or in the form of a pharmacologically acceptable salt.

A preferred dopaminergic antagonist useful in the process of this invention is haloperidol.

The dopaminergic antagonists used in the process of this invention may be administered orally, parenterally, such as by intravenous or periorbital injection, or topically by instillation into he eye.

The method of administration of the dopaminergic antagonists is adapted to the condition of the patient. At the time of the surgical procedure for cataract extraction, the drugs may be administered parenterally, e. g. by intravenous or inramuscular injection, and preferably by periorbital injection for maximum efficacy. After the surgical procedure, the patient will normally have to continue to receive the medication for several months; accordingly topical or oral administration is preferred for this phase of the treatment. The dose used will vary with the effectiveness of the individual drug as a dopaminergic anagonist. Since these drugs have long been used for their psychopharmacological effect, which is known to be the result of their dopaminergic antagonism, effective amounts of each individual drug are well known. Long term therapy may be accomplished by administration of the drug orally, in the form of capsules, tablets, suspensions, and the like, or by topical administration to the eye in a suitable ophthalmologically acceptable vehicle. A suitable topical composition comprises an effective amount of the drug in a buffered isotonic saline aqueous solution, suitable for instillation. Alternatively, the drug may be formulated in an ophalmologically acceptable ointment. Should the particular drug being used exhibit poor absorption when used topically in the eye, an absorption promoter such as dimethyl sulfoxide may be incorporated into the vehicle. The concentration of the drug in the ophthalmologic vehicle will vary with the potency of the compound, but will typically be between 0.1 and 100 mg/ml of vehicle. For the preferred drug, haloperidol, a preferred concentration range is from about 2 to about 40 mg/ml, and the most preferred concentration is about 2 mg/ml in a buffered aqueous solution. This solution may be used for injection or applied topically to the eye. A typical dosage regimen for long term therapy would be one drop of the topical preparation four times per day. Formulation of suitable dosage forms is entirely conventional and is well within the capability of the skilled practitioner referring to standard pharmacy references such as., e. g., Remington's Practice of Pharmacy, A. Osol, Ed., Mack Publishing Co., Easton, Pa.

It is preferred that the dopaminergic antagonist be administered beginning immediately after a procedure for catarct extraction or even during the operation and that the administration be continued for a period of several months in order to prevent the onset of cystoid macular edema. However, it is also according to the invention to treat patients who have already developed CME in order to cure the disease.

While the inventor does not wish to be bound by theoretical considerations, it is believed that the presence of dopamine in the retina, secreted as a consequence of stimulation of dopaminergic neurons by the surgical trauma, particularly by tension placed on the retina at its points of attachment to the vitreous, may be at least one contributing cause of the edema. It is known that dopamine can increase the permeability of capillary walls, an effect which may contribute to the leakage of fluid from the retinal capillaries to form the characteristic cysts of CME.

Because dopaminergic antgonists have other effects, and particularly psychopharmaceutical affects, it is desirable to avoid these effects as far as possible by keeing the dose as low as possible. For example, haloperidol, a preferred dopaminergic antagonist of this invention, has strong tranquilizing effects and is also particularly prone to cause extrapyramidal discharges.

It has now been found that the activity of haloperidol is potentiated by the presence of ascorbic acid, as discussed in G. V. Rebec et al., Science 227, 438–440 (1985). Accordingly, in a preferred embodiment of the invention, in order to keep the systemic effects of the antidopaminergic drug as small as possible while retaining maximum efficacy in the eye, both a dopaminergic antagonist and ascorbic acid are administered to the eye for prevention and/or treatmen of retinal edema, particularly of cystoid macular edema. If both drugs are administered topically to the eye, the amount of dopaminergic antagonist can be reduced, so that smaller amounts of the psychopharmaceutical compound are transferred to the general circulation. In another embodiment, one of the drugs may be given systemically, while the other is administered topically to the eye. In, this way it is possible, for example, to administer the dopaminergic antagonist systemically, e. g., by oral administration, in amounts too small to cause psychological effects, while at the same time administering ascorbic acid to the eye to potentiate the activity of the dopaminergic antagonist at that site to perform the desired anti-edema function. Alternatively, the dopaminergic antagonist can be administered topically to the eye, e. g., by instillation or injection, and the ascorbic acid can be administered systemically. In this embodiment, the dose of dopaminergic antagonist to the eye can be reduced, so that side effects caused by the drug entering the general circulation are proportionally reduced.

The invention having now been fully described, it will be apparent to one skilled in the art that many variations and modifications may be made therein without departing from the spirit or scope of the invention.

What is claimed is:

1. A method of prevening retinal edema due to accumulated fluid leaking from capillary vessels comprising administering to a patient in need thereof a preventive effective amount of a dopaminergic antagonist selected from the group consisting of phenothiazine derivatives: thioxanthines, dibenzoxepines and butyrophenones to prevent said edema together with an amount of ascorbic acid effective to potentiate the activity of said dopaminergic antagonist.

2. The method of claim 1 wherein said dopaminergic antagonist is administered topically to the eye.

3. The method of claim 1 wherein said dopaminergic antagonis is haloperidol.

4. The method of claim 3, wherein said haloperidol is topically administered to the eye in a buffered isotonic aqueous saline solution containing from about 2 to about 40 mg/ml of haloperidol.

5. The method of claim 4 wherein said solution contains about 2 mg/ml of haloperidol.

6. A method for preventing cystoid macular edema due to accumulated fluid leaking from capillary vessels comprising administering to a patient in need thereof a preventive effective amount of a dopaminergic antagonist selected from the group consisting of phenothiazine derivatives: thioxanthines, dibenzoxepines and butyrophenones to prevent said edema together with an amount of ascorbic acid effective to potentiate the activity of said dopaminergic antgonist.

7. The method of claim 6 wherein said dopaminergic antagonist is administered topically to the eye.

8. The method of claim 6 wherein said dopaminergic antagonist is haloperidol.

9. The method of claim 8, wherein said haloperidol is topically administered to the eye in a buffered isotonic aqueous saline solution containing from about 1 to about 40 mg/ml of haloperidol.

10. The method of claim 9 wherein said solution contains about 2 mg/ml of haloperidol.

11. The method of claim 6 wherein said patient has undergone a surgical procedure for cataract extraction and said dopaminergic antagonist and said ascorbate are administered post operatively.

12. The method of claim 6 wherein said ascorbic acid is administered topically to the eye.

13. The method of claim 12 wherein said ascorbic acid is administered in a buffered isotonic saline solution containing from about 0.2 mg/ml to about 40 mg/ml of ascorbic acid.

14. The method of claim 12 wherein said dopaminergic antagonis is haloperidol and said haloperidol is topically administered to the eye in a buffered isotonic aqueous saline solution containing from about 2 mg/ml to about 40 mg/ml of haloperidol and from about 0.2 mg/ml to about 40 mg/ml of ascorbic acid.

15. The method of claim 14 wherein both said dopaminergic antagonist and said ascorbic acid are administered topically to the eye.

16. The method of claim 15 wherein said dopaminergic antagonist is administered systemically and said ascorbic acid is administered topically to the eye.

17. The method of claim 16 wherein said dopaminergic antagonist is administered topically to the eye and said ascorbic acid is administered systemically.

18. A method for treating retinal edema due to accumulaated fluid leaking from capillary vessels comprising administering to a patient afflicted with retinal edema a therapeutically effective amount of a dopaminergic antagonist to reduce said edema together with an amount of ascorbic acid effective to potentiate the activity of said dopaminergic antagonist.

19. The method of claim 18 wherein said dopaminergic antagonist is administered topically to the eye.

20. The method of claim 18 wherein said dopaminergic antagonist is haloperidol.

21. The method of claim 20 wherein said haloperidol is topically administered to the eye in a buffered isotonic aqueous saline solution containing from about 2 to about 40 mg/ml of haloperidol.

22. The method of claim 21 wherein said solution contains about 2 mg/ml of haloperidol.

23. A method for treating cystoid macular edema due to accumulated fluid leaking from capillary vessels comprising administering to a patient afflicted with said edema a therapeutically effective amount of a dopaminergic antagonist to reduce said edema together with an amount of ascorbic acid effective to potentiate the activity of said dopaminergic antagonist.

24. The method of claim 23 wherein said dopaminergic antagonist is administered topically to the eye.

25. The method of claim 23 wherein said dopaminergic antagonist is haloperidol.

26. The method of claim 25 wherein said haloperidol is topically administered to the eye in a buffered isotonic aqueous saline solution containing from about 2 mg/ml to about 40 mg/ml of haloperidol.

27. The method of claim 26 wherein said solution contains about 2 mg/ml of haloperidol.

* * * * *